US011337483B2

(12) United States Patent
Segura et al.

(10) Patent No.: US 11,337,483 B2
(45) Date of Patent: May 24, 2022

(54) METHOD AND APPARATUS FOR A SAFETY BEACON FOR A WELDING PROTECTION DEVICE

(71) Applicant: Illinois Tool Works Inc., Glenview, IL (US)

(72) Inventors: Ricardo Segura, Lake in the Hills, IL (US); Joseph C. Schneider, Menasha, WI (US)

(73) Assignee: Illinois Tool Works Inc., Glenview, IL (US)

( * ) Notice: Subject to any disclaimer, the term of this patent is extended or adjusted under 35 U.S.C. 154(b) by 308 days.

(21) Appl. No.: 16/573,053

(22) Filed: Sep. 17, 2019

(65) Prior Publication Data

US 2020/0085132 A1   Mar. 19, 2020

Related U.S. Application Data

(60) Provisional application No. 62/732,025, filed on Sep. 17, 2018.

(51) Int. Cl.
| | |
|---|---|
| *A42B 3/22* | (2006.01) |
| *A42B 1/242* | (2021.01) |
| *A42B 3/30* | (2006.01) |
| *G08B 7/06* | (2006.01) |
| *F21V 33/00* | (2006.01) |
| *H05B 47/10* | (2020.01) |
| *H05B 47/105* | (2020.01) |
| *A61F 9/06* | (2006.01) |
| *H05B 47/16* | (2020.01) |

(52) U.S. Cl.
CPC .............. *A42B 3/225* (2013.01); *A42B 1/242* (2013.01); *A42B 3/30* (2013.01); *A61F 9/06* (2013.01); *F21V 33/0004* (2013.01); *G08B 7/06* (2013.01); *H05B 47/10* (2020.01); *H05B 47/105* (2020.01); *H05B 47/16* (2020.01)

(58) Field of Classification Search
CPC ....................................... A42B 3/225
See application file for complete search history.

(56) References Cited

U.S. PATENT DOCUMENTS

| | | | | |
|---|---|---|---|---|
| D296,832 S | * | 7/1988 | Bachik ......................... | D29/110 |
| 7,934,846 B1 | * | 5/2011 | Schwanz ................... | F21L 4/04 |
| | | | | 362/106 |
| 8,721,103 B2 | * | 5/2014 | Robinson ............ | F21V 23/0492 |
| | | | | 362/105 |
| 9,629,752 B1 | * | 4/2017 | Graham .................. | A61F 9/067 |
| 10,251,787 B2 | * | 4/2019 | Currie ...................... | A61F 9/067 |
| D858,000 S | * | 8/2019 | Zartler ......................... | D29/110 |

(Continued)

FOREIGN PATENT DOCUMENTS

| | | |
|---|---|---|
| DE | 102005032136 | 1/2007 |
| KR | 101237675 | 8/2012 |

OTHER PUBLICATIONS

Int'l Search Report and Written Opinion Appln. No. PCT/US2019/051475 dated Nov. 27, 2019 (11 pgs).

*Primary Examiner* — Travis R Hunnings
(74) *Attorney, Agent, or Firm* — McAndrews, Held & Malloy, Ltd.

(57) ABSTRACT

A protection device is disclosed, where the protection device comprises an eye protection shield, a light beacon, and a control circuitry to control the light beacon.

20 Claims, 5 Drawing Sheets

(56) References Cited

U.S. PATENT DOCUMENTS

| | | | | |
|---|---|---|---|---|
| 2007/0261153 A1* | 11/2007 | Wise | ............ | A42B 3/166 |
| | | | | 2/423 |
| 2011/0107491 A1* | 5/2011 | Sanders | ............ | A61F 9/06 |
| | | | | 2/8.2 |
| 2016/0022496 A1* | 1/2016 | DeKeuster | ...... | G02F 1/13306 |
| | | | | 349/14 |
| 2018/0271709 A1* | 9/2018 | Currie | ............ | A61F 9/067 |
| 2019/0333178 A1* | 10/2019 | Cheng | ............ | G06Q 10/20 |
| 2020/0000168 A1* | 1/2020 | Patel | ............ | F21V 21/145 |

\* cited by examiner

METHOD AND APPARATUS FOR A SAFETY BEACON FOR A WELDING PROTECTION DEVICE

BACKGROUND

The present disclosure relates to a welding protection device for a user, and more particularly, to a method and apparatus for a safety beacon for a welding protection device.

Limitations and disadvantages of conventional systems for a welding protection device, such as, for example, welding helmets, welding goggles, etc., will become apparent to one of skill in the art, through comparison of such approaches with some aspects of the present method and system set forth in the remainder of this disclosure with reference to the drawings.

SUMMARY

Methods and systems are provided for a safety beacon for a welding protection device, substantially as illustrated by and described in connection with at least one of the figures, as set forth more completely in the claims.

BRIEF DESCRIPTION OF THE DRAWINGS

These and/or other aspects will become apparent and more readily appreciated from the following description of some examples of the disclosure, taken in conjunction with the accompanying drawings.

The drawings are not necessarily to scale. Where appropriate, similar or identical reference numbers are used to identify similar or identical elements.

DETAILED DESCRIPTION

A welding protection device is used to protect the welder from the intense heat and brightness generated by a welding torch in use. However, it may be useful to be able to warn others of ongoing welding work at a location to keep other people from wandering too close to the work area. Accordingly, various aspects of the disclosure are presented to provide visual warning with a light beacon, as well as with audio warning via a speaker.

Figure 1A:
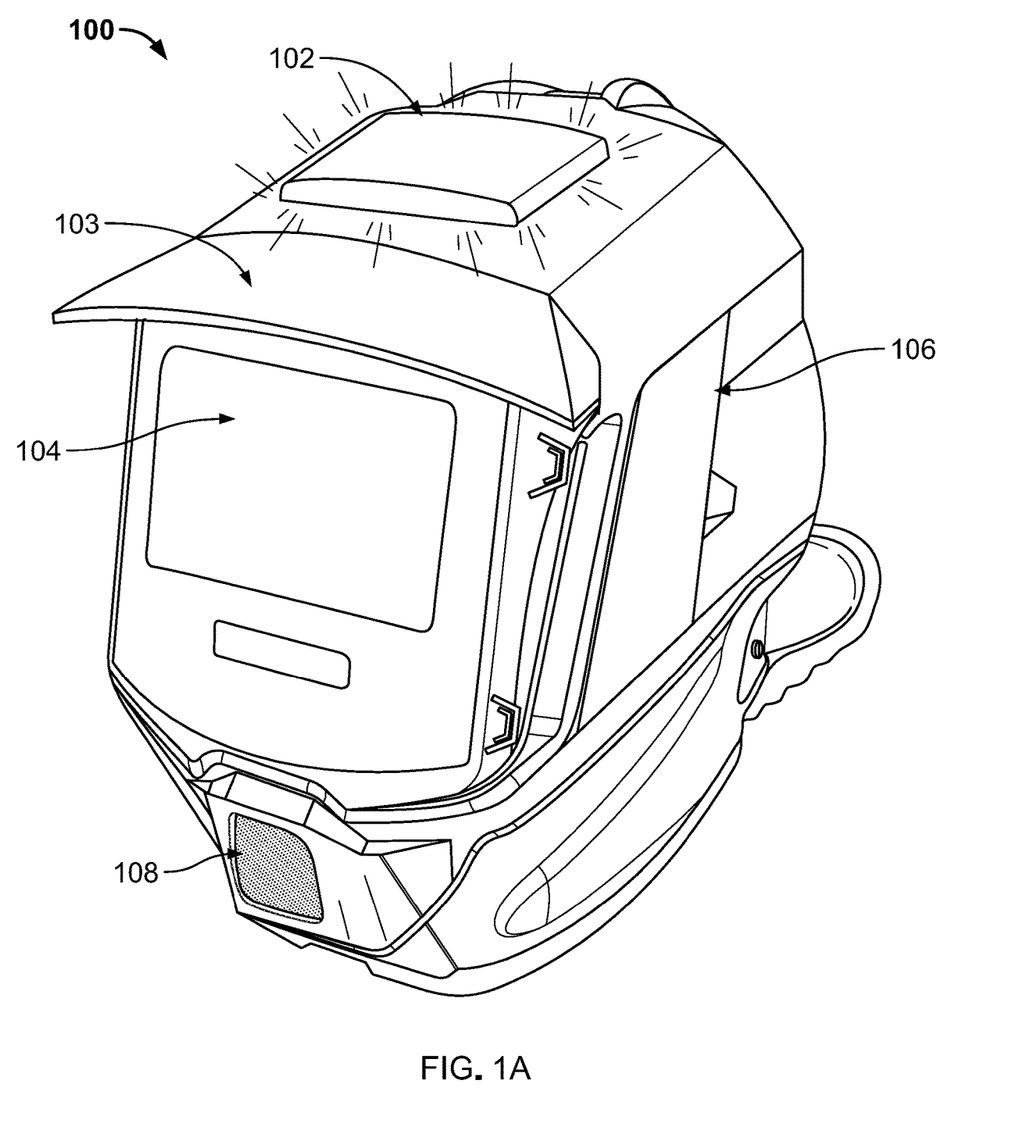
FIG. 1A is a drawing of an example welding protection device with a first example of a light beacon, in accordance with aspects of the disclosure.

FIG. 1A illustrates an example welding protection device 100 that comprises a light beacon 102A and an eye protection shield 104. There is also shown a visor 103, control circuitry 106, and a speaker 108.

The light beacon 102A may be, for example, a light reflecting device, light emitting device, or a combination of a light reflecting device and a light emitting device. While FIG. 1A shows the light beacon 102A as a single beacon, other aspects of the disclosure may have multiple light beacons. The light beacon 102A may comprise one or more light emitting devices and/or light reflecting devices. For example, the light beacon 102A may comprise one or more LEDs, light bulbs, reflective devices, and/or any other suitable light emitting device and/or light reflecting device.

In FIG. 1A, the light beacon 102A is located at the top of the welding protection device 100. This allows the emitted light from the light beacon 102A to be seen in substantially all directions around the welding protection device 100. The light may be emitted in all 360° or the light may be emitted in a portion of 360° such that the emitted light can be seen from substantially all directions in line of sight of the light beacon and/or a welding arc from a welding torch used by the welder that is wearing the welding protection device 100. For example, the light from the light beacon 102A may comprise a plurality of light rays such that the light beacon 102A is visible from substantially all directions. Accordingly, the emitted light may be said to be emitted in substantially all directions. For example, the light beacon 102A may emit light on all sides and/or on top, or the light beacon 102A may emit light at a portion of each side and/or on top.

Other examples may allow placement of the light beacon 102A, which may comprise a plurality of light beacons, at other parts of the welding protection device 100. For example, the light beacon 102A may be placed toward the rear of the top portion of the welding protection device 100, or several light beacons 102A at various locations around the circumference of the welding protection device 100. The light beacon 102A may be at a rear portion of the welding protection device 100, for example, for the occasions when the workpiece being welded is large enough to block the area in front of the workpiece. Accordingly, the light beacon 102A may be placed at a different part of the welding protection device 100. The light beacon 102A may be, for example, removed and moved to different positions or moved along a predetermined path such as a groove or a rail.

The light beacon 102A may be secured to the welding protection device 100 by any appropriate method. For some aspects of the disclosure that utilizes permanent placement, the light beacon 102A may be integrated into or on to the welding protection device 100. For those aspects of the disclosure that utilizes movable light beacon 102A, the light beacon 102A may be, for example, magnetically secured, via a latch or a holding mechanism, via an arm riding in a groove where an end of the arm in the groove prevents the welding protection device 100 from falling out, via an arm riding on a rail, etc. There may be a screw that can be used to tighten the arm at the desired location of the groove or rail. The arm may also have a clamping mechanism that expands when the clamping mechanism is released to secure the light beacon 102A to the groove, or the clamping mechanism tightens when released to grip the rail to secure the light beacon 102A. The light beacon 102A may also be secured to the welding protection device 100 by, for example, hook-and-loop fasteners. Therefore, various aspects of the disclosure can use any of the different types of fasteners that is suitable.

The light beacon 102A is provided with power by one or more of various power sources (not shown). For example, the light beacon 102A may have a battery located as a part of the light beacon 102A. Additionally or alternatively, the light beacon 102A may be provided power by a battery pack mounted on or in the welding protection device 100. The light beacon 102A may also be provided power by a remote power source that is carried by the welder, such as, for example, a battery pack that is attached to equipment carried or used by the welder, or clothes or belt worn by the welder. The light beacon 102A may also receive power from a remote power source that is not carried by the welder. For example, the power source may provide power via a power line to the welding protection device 100 or the light beacon 102A, or wirelessly to the welding protection device 100 or the light beacon 102A. When the power is provided to the welding protection device 100, the light beacon 102A may be powered, for example, by a power line from the welding protection device 100.

In some examples of the disclosure, the light beacon 102A may not be removable, while in other examples of the disclosure may have removable light beacons 102A. The removable light beacon 102A may be tethered to the welding protection device 100 or may be completely separable so that it can be placed on another object. In some examples, only a portion of the light beacon 102A may be removable. This may allow, for example, use of a portion of the light beacon 102A on the welding protection device 100 as well as having another portion of the light beacon 102A on another object.

The visor 103 may be configured to block at least some of the light emitted by the light beacon 102A from affecting, for example, an auto-darkening feature for a welding helmet. While an example visor 103 is shown, other visors 103 may have different shapes and/or dimensions. In some examples of the disclosure, the visor 103 may be permanently mounted to the welding protection device 100 or a part of the welding protection device 100, while other examples of the disclosure may have the visor 103 removably attached to the welding protection device 100. The visor 103 may be attached to the top of the welding protection device 100 or to the eye protection shield 104. The visor 103 may also comprise, for example, a structure near a light sensor (not shown) used for the auto-darkening feature to block light from the light beacon 102. For example, the visor 103 may be a lip above a light sensor when the light sensor is below the light beacon 102. The control circuitry 106 and the speaker 108 are described in more detail with respect to FIGS. 1C and 2.

The eye protection shield 104 may be any shield that protects a welder's eyes. For example, the eye protection shield 104 may be a welding face shield that can be raised or lowered to cover the welder's eyes and/or face, welder's goggles/glasses that protect the welder's eyes, etc. Accordingly, when the visor 103 is attached to the welding protection device 100, the eye protection shield 104 may be configured to be raised, for example, over the light beacon 102A and the visor 103.

In various aspects of the disclosure, the light beacon 102A may be turned on when a sensor detects a first appropriate input and turned off when the sensor detects a second appropriate input. For example, a motion detector, a proximity sensor, a switch, etc. may detect that the welding protection device 100 has been put on or taken off by the welder, and respectively turn on or turn off the light beacon 102A. Similarly, a motion detector, a proximity sensor, a switch, etc., may detect that the eye protection shield 104 has been lowered or raised by the welder, and respectively turn on or turn off the light beacon 102A. A camera may also be used where the image(s) can be processed to determine the appropriate first and second appropriate inputs. Some welding protection device 100 may have an auto-darkening feature for the eye protection shield 104. The light beacon 102A may use a similar input where an intensity of light from a welding torch (not shown) may be sensed to turn on the light beacon 102A, and turn off the light beacon 102A when the welding torch is, for example, shut off. When the auto-darkening feature of the eye protection shield 104 is controlled by an external device, such as, for example, a control circuitry 200 of FIG. 2, a control signal for auto-darkening the eye protection shield 104 may also be used to control the light beacon 102A.

Figure 1B:
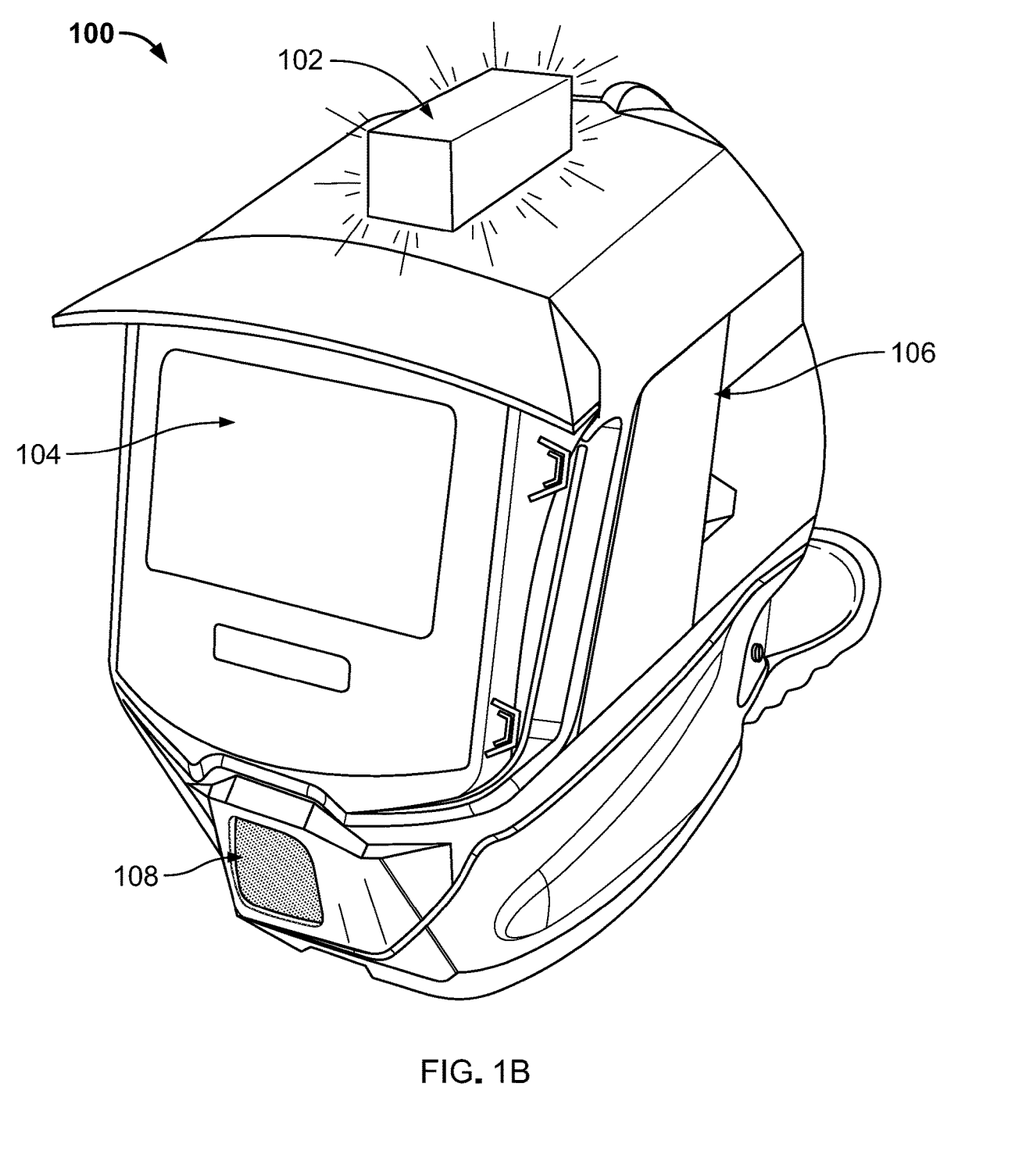
FIG. 1B is a drawing of another example welding protection device with a second example of a light beacon, in accordance with aspects of the disclosure.

FIG. 1B is a drawing of the example welding protection device 100 with a differently shaped light beacon 102B. Referring to FIG. 1B, the welding protection device 100 is similar to the welding protection device 100 of FIG. 1A except for the shape of the light beacon 102B. While FIG. 1A shows the light beacon 102A with a lower profile, the light beacon 102B has a higher profile. Accordingly, various aspects of the disclosure provides that the shape of a light beacon 102, examples of which are at least 102A and 102B, round, oval, or any shape that allows light from the light beacon 102, whether reflected or emitted, to be seen by others around the welder. For example, the light beacon 102 may be as shown in FIGS. 1A and 1B, or the light beacon 102 may be round. Another example of the light beacon 102 may be a rotating light, whether the light emitting device is rotating, or the light is reflected or controlled to have it shine for at least a portion of 360°.

It should be understood that example welding protection device 100 may comprise the visor 103, whether the visor 103 is removably mounted or permanently mounted, or an example welding protection device 100 may not have a visor 103 if it is not needed because the welding protection device 100 does not have an auto-darkening feature or because the visor is local to just around the light sensor for the auto-darkening feature.

Figure 1C:
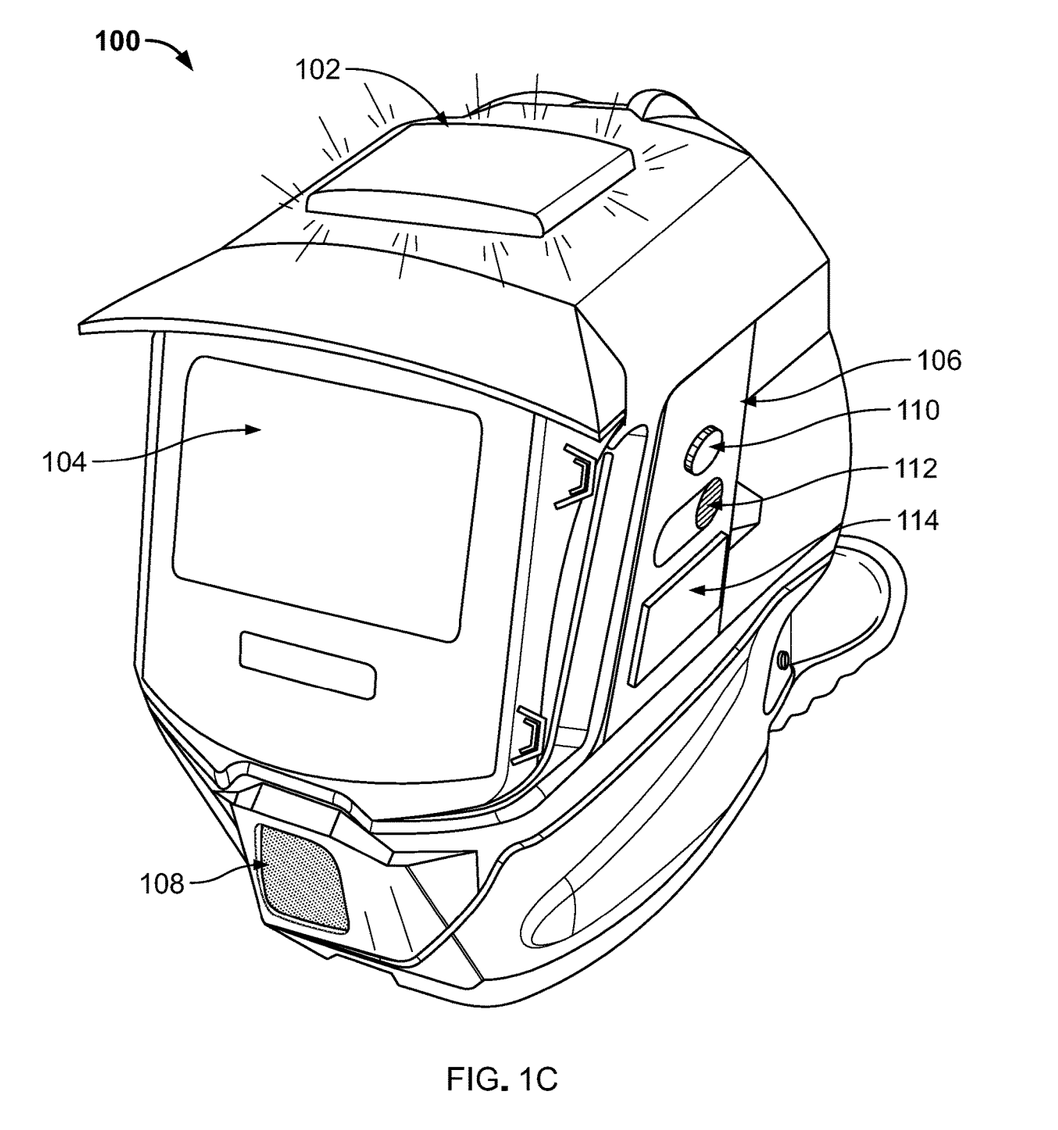
FIG. 1C shows a drawing of an example control circuitry on the welding protection device in accordance with aspects of the disclosure.

FIG. 1C is a drawing of the example welding protection device 100 with control circuitry 106 for controlling the light beacon 102 and a speaker 108. The control circuitry 106 may allow turning on/off the light beacon 102, flashing the light emitted by the light beacon 102, etc. The light beacon 102 may be one of the light beacons 102A or 102B, or any similar light beacon. The control circuitry 106 may comprise, for example, one or more input devices such as one or more rotatable knobs 110, and one or more switches 112, which may comprise, for example, push-button switch(es), toggle switch(es), etc. The control circuitry 106 may also comprise other types of input devices such as, for example, a touch sensitive panel 114 that may incorporate the functionalities of the rotatable knob(s) 110 and the switch(es) 112.

The control circuitry 106 may also be used to adjust an intensity of the light emitted by the light beacon 102. The intensity may be controlled by, for example, the slide switch 112 or the rotatable knob 110. Additionally or alternatively, the control circuitry 106 may control aspects of the light beacon 102 based on the local environment and/or activity near the welding protection device 100. For example, if there is a low ambient light, the control circuitry 106 may automatically reduce the intensity of the light beacon 102. Conversely, if there is a brighter ambient light, the control circuitry 106 may automatically increase the intensity of the light beacon.

While the control circuitry 106 is shown on the left cheek portion of the welding protection device 100, various aspects of the disclosure may have the control circuitry 106 at any one of various locations on the welding protection device 100 or on multiple locations of the welding protection device 100. For example, there may be a first control circuitry 106 on the left cheek of the welding protection device 100 as shown in FIGS. 1A-1C and a second control circuitry 106 on the right cheek of the welding protection device 100. The multiple control circuitries 106 on a welding protection device 100 may allow for easier manipulation of control devices when the user is wearing, for example, bulky welding gloves or other protection.

The control circuitry 106 may also be inside the welding protection device 100, and may comprise touch sensitive control devices % The touch sensitive control devices may be, for example, the touch sensitive panel 114.

Figure 2:
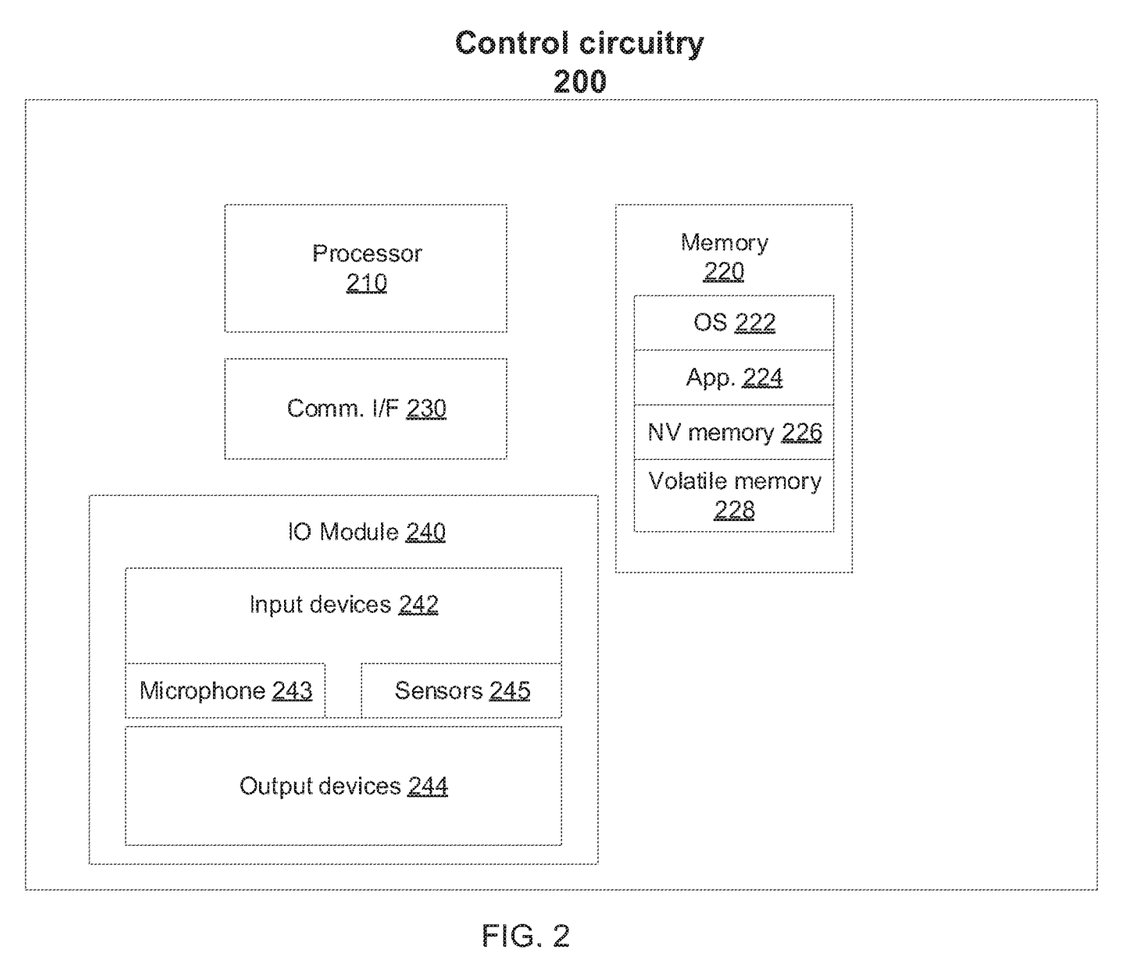
FIG. 2 is a drawing of an example control circuitry in accordance with aspects of the disclosure.

While the control circuitry 106 has been described as being on the welding protection device 100, various examples of the disclosure may also provide for the control circuitry 106 to be external to the welding protection device 100 in place of, or in addition to, being on the welding protection device 100. This may allow, for example, larger control devices that can be more easily manipulated by a user wearing, for example, bulky welding gloves. The external control circuitry 106 may communicate with the control circuitry 106 on the welding protection device 100 via wireless or wired communication using, for example, communication interface 230 (FIG. 2).

The control circuitry 106 may further control the flashing of the light. For example, to turn off the flashing to have a steady light, or to turn on the flashing. Accordingly, various aspects of the disclosure may have the light beacon 102 that can turn on or off, and other aspects of the disclosure may have the light beacon 102 that can also flash the light beacon 102 when it is turned on.

When the light beacon 102 is controlled to emit flashing light, the control circuitry 106 may also be able to control a duty cycle of the flashing light, where the duty cycle indicates the duration of the period when the light is turned on and the duration of the period when the light is turned off. The flashing light may also change from a first intensity of light to a second intensity of light. The flashing light may also brighten over a period of time and then dim over a period of time. Accordingly, the duty cycle may control the time that the flashing light is at the first intensity, which may be when the light is turned off or at some light level, and the time that the flashing light is at the second intensity. Therefore, the duty cycle may also indicate the brightening period and the dimming period. Various aspects of the disclosure may have a default duty cycle for the flashing light.

As the control circuitry 106 may be used to control the flashing light periods, some aspects of the disclosure may keep a previously selected duty cycle. Accordingly, if the default duty cycle is not changed, then the default duty cycle is used when the light beacon 102 is turned on and set to flash. Various example control circuitry 106 may be able to store several duty cycles, including the default duty cycle, and the user may select one of those duty cycles. Some examples of selecting a duty cycle may be, for example, rotating a knob to control a duration of a period when flashing light is on, moving a slide switch to control a duration of a period when flashing light is on, touching a touch panel on the control circuitry 106 to control a duration of a period when flashing light is on, pushing a button repeatedly, pushing one of several buttons, speaking a command (for example, "50% duty cycle"), etc. Accordingly, the duty cycle may be changed, for example, via the control circuitry 106, where the control circuitry 106 may comprise using any appropriate methods/devices that are known or may be developed in the future.

Various aspects of the disclosure may also have the light beacon 102 emit different colors of lights. For example, the light beacon 102 may emit a first color light for a first period of time, then a second color light for a second period of time, etc., where the first and second periods of time may be fixed or variable. The colors emitted and the durations of the first and second periods may have default values, which may be changed, for example, via the control circuitry 106 using any appropriate methods/devices that are known or will be developed in the future.

Additionally, with some aspects of the disclosure, the welding protection device 100 may have a light beacon 102 that can flash lights that are different colors where the period during which the lights may be off may also be adjustable. Furthermore, one or more colors may be selected to flash multiple times before the next color light is emitted. Accordingly, the control circuitry 106 may be able to control the light beacon 102 to provide various light patterns with the duty cycle as described above.

The control circuitry 106 may also control output of various sounds or sound patterns, such as, for example, words, sirens, etc., via the speaker 108. The control circuitry 106 may be able to turn the speaker 108 off or turn the speaker 108 on to output the various sounds or sound patterns. Turning the speaker 108 on may comprise providing electrical input to be converted to sound, or may comprise controlling circuitry such as, for example, amplifier circuitry (not shown) for the speaker 108. The amplifier circuitry may be, for example, part of the control circuitry 106.

The control circuitry 106 may also control, for example, the volume of sound output by the speaker 108. The sound volume may be controlled, for example, by a rotatable knob 110, a switch(es) 112 such as a slide switch, push-button switch, etc. The sound volume may also be, for example, controlled automatically by the control circuitry 106 depending on the ambient sound detected by, for example, the input devices 242 (FIG. 2), which may comprise a microphone 243. For example, with respect to FIG. 2, the processor 210 may process the detected sound to determine the output sound volume of the speaker 108.

The speaker 108 is shown in FIG. 1C as being near the chin portion of the welding protection device 100. However, various aspects of the disclosure may have the speaker 108 at other parts of the welding protection device 100, and there may be more than one speaker 108 on the welding protection device 100.

In various aspects of the disclosure, the speaker 108 may emit warning sounds when the light beacon 102, 102A, or 102B is turned on.

The control circuitry 106 is described in more detail with respect to FIG. 2. The visor 103 is not shown in FIG. 1C, however, it should be understood that the example welding protection device 100 may comprise the visor 103, whether the visor 103 is removably mounted or permanently mounted.

FIG. 2 shows a block diagram of an example control circuitry in accordance with various aspects of the disclosure. Referring to FIG. 2, there is shown an example control circuitry 200 that may be used in various aspects of the disclosure. The control circuitry 200 may comprise, for example, a processor 210, memory 220, a communication interface 230, and an IO interface 240. The processor 210 may comprise, for example, one or more processors.

The memory 220 may include non-volatile memory 226 and volatile memory 228. The storage described for holding local data may be part of the memory 220 or comprise separate memory. The operating system 222 and applications 224 may be stored in, for example, the non-volatile memory 226, and may be copied to volatile memory 228 for execution by the processor 210. Various aspects of the disclosure may use different memory architectures that are design and/or implementation dependent. For example, some aspects of the disclosure may have the operating system 222 and applications 224 in the non-volatile memory 226 executed at least in part from the non-volatile memory 226.

The communication interface 230 may allow the control circuitry 200 to communicate with other devices via, for example, a wired protocol such as USB, Ethernet, Firewire, etc., or a wireless protocol such as Bluetooth, Near Field Communication (NFC), Wi-Fi, etc. The wired or wireless protocol may also be, for example, a proprietary protocol. The various types of radios for communication may be referred to as a transceiver for the sake of simplicity. The communication may be, for example, with various sensors and/or devices that can relay sensor data. The communication interface 230 may also be used to communicate with other networks such as local networks, cellular networks, etc.

The control circuitry 200 may also comprise the IO module 240 for communication with a user via the input devices 242 and output information to be displayed on output devices 244. The input devices 242 may comprise, for example, switches, slide switches, membrane switches, buttons, touch sensitive screen, which may be a part of a display, a microphone 243, etc. The touch sensitive screen may have soft buttons, switches, slide switches, etc. that emulate their physical counterparts. The input devices 242 may also comprise, for example, various sensors 245, cameras, etc. The output devices 244 may comprise, for example, display(s), speaker(s), LED(s), vibration motor(s), etc. Support circuitry for the various output devices 244 may also be considered a part, of the output devices 244. For example, the support circuitry for the speaker 244 may comprise a digital-to-analog converter, an amplifier, etc. Accordingly, in some aspects of the disclosure, the light beacon 102, 102A, or 102B may be thought of as being logically grouped with the control circuitry 200. In other aspects of the disclosure, the light beacon 102, 102A, or 102B may not be logically grouped with the control circuitry 200.

The processor 210 may operate using different architectures in different examples. For example, the processor 210 may use the memory 220 to store instructions to execute, or the processor 210 may have its own memory (not shown) for its instructions.

Various examples of the disclosure may use other architectures where the different functionalities may be grouped differently. For example, the grouping may be in different integrated circuit chips. Or, the grouping may combine different devices such as the IO module 240 and the communication interface 230 together, etc. Additionally, the control circuitry 200 may refer logically to various physical devices. For example, one or more of the output devices 244 may be at a different location than one or more of the input devices 242.

While various physical devices, including a touch panel, have been described as controlling various functions of the welding protection device 100, voice may also be used to give commands to control the various functions. The voice input may be received by, for example, a microphone 243 that is a part of the input devices 242 of the control circuitry 200. The digitized commands may be processed by, for example, the processor 210 to determine the specific command. The specific command may then be used to control the light beacon 102, 102A, or 102B and/or the speaker 108.

The software for voice recognition may be part of, for example, the operating system 222 and/or the applications 224 in the memory 220.

Additionally, while power sources may generally be grouped separately from the control circuitry 200, various aspects of the disclosure may group a power source with the control circuitry 200. For example, receiving power wirelessly or via wire, and then providing power to the light beacon 102, 102A, or 102B, may be considered to be a function of the I/O module 240 where, for example, the input devices 242 receives the power and manages the power to be provided to the light beacon 102, 102A, or 102B.

Various aspects of the disclosure may also comprise a notification system where the control circuitry 200 is configured to provide visual and/or audible notification to the user of the welding protection device 100 when the light beacon 102 and/or the speaker 108 is turned on. For example, when the light beacon 102 is turned on, an LED (not shown) may be turned on so that it is visible to the user. The LED may be inside the welding protection device 100 or external to the welding protection device 100. The LED may be on steadily or blink at some rate, where one of the rates may be, for example, the same rate as the flashing by the light beacon 102. Various aspects of the disclosure may also provide visual notification by allowing a reflection of the light from the light beacon 102 to be visible to the user. For example, a reflection of the emitted light may be provided to be visible to the user, or a portion of the emitted light may guided to be visible to the user.

The emitted light may be reflected, for example, via a mirror, a portion of the eye protection shield 104, or any suitable material that reflects light. The light guide for the emitted light may be, for example, an optical fiber or a similar device. The light guide may also be, for example, a path through the welding protection device 100 that allows a portion of the emitted light to be visible at the interior of the welding protection device 100. The light beacon 102 may provide light that is directed toward the interior of the welding protection device 100 via, for example, a hole in the welding protection device 100, a transparent portion of the welding protection device 100, etc.

Various aspects of the welding protection device 100 may allow the audible output of the speaker 108 to be heard by the user wearing the welding protection device 100. Various aspects of the welding protection device 100 may also provide a speaker that may be in the interior of the welding protection device 100 or exterior to the welding protection device 100 to provide notification to the user. The audible notification to the user may be the same audible warning output by the speaker 108 or some other type of audible notification. For example, the audible notification may be a repeated sound, or a repeated phrase.

Accordingly, the control circuitry 200 may allow notification via light and/or sound. The control circuitry 200 may also allow controlling the intensity of the notification light or the volume of the notification sound, as well as a particular pattern of each. The notification may be controlled by devices similar to those that allow controlling of the light beacon 102 and/or the speaker 108.

Various aspects of the disclosure may also provide tactile notification to the user via a vibration motor that may be a part of the output devices 244. The vibrations may indicate to the user that sound and/or light are being emitted from the welding protection device 100. Turning on the vibration motor, adjusting the intensity of the vibration, and patterns of the vibration may also be controlled by control devices similar to those described for controlling the light beacon 102 and/or the speaker 108. Accordingly, feedback to the user of when the light beacon 102 is emitting light and/or the speaker 108 is emitting sound may be provided by vibration, sound, or light.

Additionally, while various aspects of the disclosure were described with respect to a welding protection device, it can be seen that the disclosure may apply to other types of protection devices. For example, various examples of the disclosure may also apply to protective used for grinding, cutting, etc., for riding motor vehicles, or other head/face protection devices.

Figure 3A:
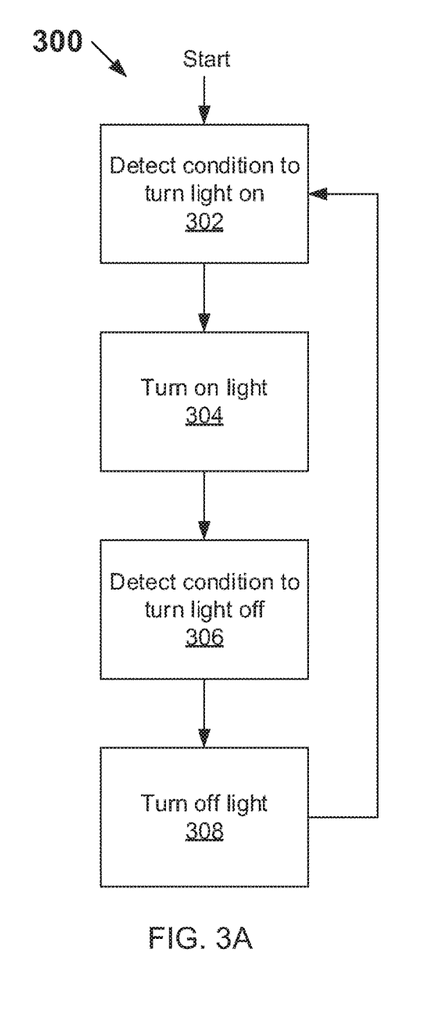
FIGS. 3A, 3B, and 3C are flow diagrams for examples of controlling a light beacon on the welding protection device in accordance with aspects of the disclosure.
Figure 3B:
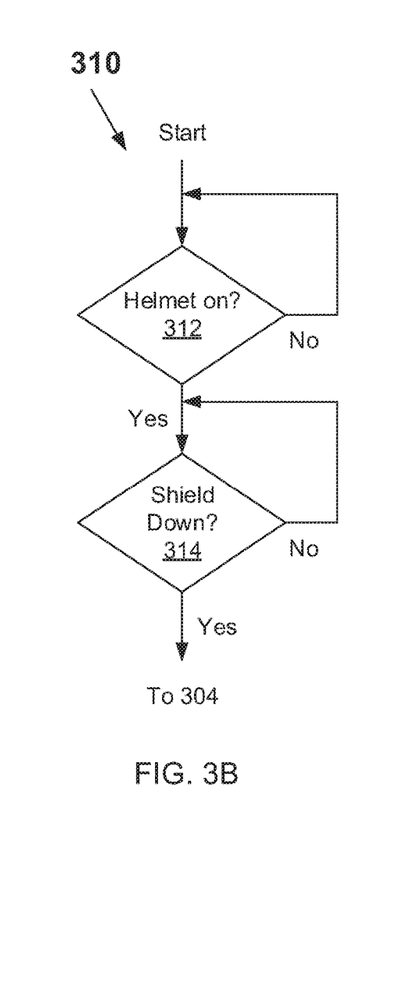
Figure 3C:
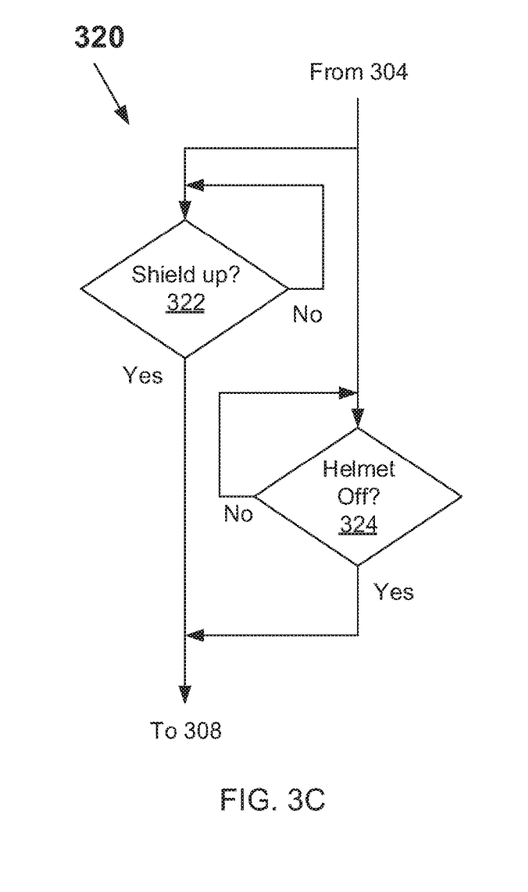

FIGS. 3A, 3B, and 3C are flow diagrams illustrating examples for controlling a light beacon on the welding protection device. FIG. 3A is an example flow diagram 300 with blocks 302 to 308. At block 302, the control circuitry 200, for example, determines whether the light beacon 102 should be turned on. When appropriate conditions are met, the control circuitry 200 turns on the light beacon 102 at block 304. Flow diagram 310 explains some of the appropriate conditions for turning on the light beacon 102.

At block 306, the control circuitry 200, for example, determines whether appropriate conditions are met to turn off the light beacon 102. When the appropriate conditions are met, the control circuitry 200 turns off the light beacon 102 at block 308. Some of the conditions for turning off the light beacon 102 is described with respect to the flow diagram 320. The next step is then to block 302 to wait for appropriate conditions to turn on the light beacon 102.

When the light beacon 102 is turned on or off in blocks 304 and 308, respectively, other functions may also be performed by the control circuitry 200. For example, sound may be emitted via the speaker 108. Additionally, light sensors 245 of the input devices 242 may detect ambient light conditions and control an intensity of light emitted from the light beacon 102. Similarly, volume of the sound from the speaker 108 may be controlled depending on ambient noise sensed by, for example, a microphone 243 that may be a part of the input devices 242. A vibrating motor may be a part of the output devices 244, and the vibrating motor may be turned on periodically or continuously to provide tactile feedback to the user that the light beacon 102 is turned on.

Additionally, the control circuitry 200 may control a duty cycle of lights emitted by the light beacon 102, where the emitted light may comprise one or more colors of light. For example, a first color may be turned on, then a second color may be turned on, etc., so that different colors may be emitted from the light beacon 102 as described above.

FIG. 3B is an example flow diagram 310, with blocks 312 and 314, for detecting appropriate conditions for turning on the light beacon 102. Accordingly, in an example of the disclosure, the flow diagram 310 may be used in place of the block 302. When the flow diagram 300 starts, there may be a determination by the control circuitry 200 whether, for example, a user has put on the welding protection device 100. This may be done in block 312 by the control circuitry 200 using, for example, sensors 245 in the input devices 242. The sensors 245 may be, for example, proximity sensors to detect a head of the user, motion sensors to detect the welding protection device being lifted and then placed on the user's head, etc. The control circuitry 200 may, for example, loop, or wait for an interrupt, etc., until it is detected that the welding protection device 100 is on the user's head.

At block 314 the control circuitry 200 may determine whether the eye protection shield 104 is in a down position. The position of the eye protection shield 104 may be determined by switches and/or sensors 245 in the input devices 242. A switch may be opened or closed when the eye protection shield 104 is in the up position or in the down position, respectively. For example, a proximity sensor may be used to determine whether the eye protection shield 104 is in the up position or in the down position. When it is determined that the eye protection shield 104 is in the down position, the control circuitry 200 may turn on the light beacon 102 in block 304. While in block 314, the control circuitry 200 may, for example, loop, or wait for an interrupt, etc., until it is detected that the eye protection shield 104 is in a down position.

While this is one aspect of the disclosure, another aspect of the disclosure may turn the beacon 102 on when the helmet is first put on the head of the user. Still other aspects of the disclosure may have a user turn on and off the light beacon 102.

FIG. 3C is an example flow diagram 320 with blocks 322 and 324, for detecting appropriate conditions for turning off the light beacon 102. Accordingly, in an example of the disclosure, the flow diagram 320 may be used in place of the block 306. When the flow diagram 320 starts, there may be a determination by the control circuitry 200 whether the eye protection shield 104 is in the up position in block 322 or whether the welding protection device 100 has been taken off the user's head in block 324. When either condition is true, the next step is to indicate that the conditions have been met to turn off the light beacon 102. Accordingly, the light beacon is turned off in block 308.

In block 322, when the control circuitry 200 determines that the eye protection shield 104 is in the down position, the control circuitry may loop, wait for an interrupt, etc., until it determines that the eye protection shield 104 is in the up position. Similarly, in block 324 the control circuitry 200 may loop, wait for an interrupt, etc., until it is determined that the welding protection device 100 has been removed from the user's head.

While the control circuitry 200 has been described as performing various functions (loop, wait for an interrupt, make determinations, etc.), it should be understood that the processor 210 executes instructions in memory 220 for performing various functions. For example, the instructions may be a part of the applications 224, or some other program that may be in the non-volatile memory 226 or the volatile memory 228.

It should be noted that any feature described for a specific figure may also apply to other figures.

Accordingly, it can be seen that the disclosure provides for a protection device that comprises an eye protection shield, a light beacon configured to emit light in substantially all directions, and a control circuitry to control the light beacon. The protection device may also comprise a visor configured to block at least some light from the light beacon from reaching a light sensor used for an auto-darkening feature for the eye protection shield. The control circuitry may be configured to turn on the light beacon at a time when the protection device is put on a user and/or at a time when the eye protection shield is in a down position. The control circuitry may be configured to turn off the light beacon when the protection device is taken off and/or when the eye protection shield is in an up position.

That is, the control circuitry may be configured to perform one or both of turn on the light beacon at a time when the protection device is on a user and turn off the light beacon when the protection device is taken off the user. The control circuitry may be configured to turn on the light beacon at a time when the eye protection shield is in a down position and turn off the light beacon when the eye protection shield is in an up position.

The control circuitry may comprise one or more control devices such as, for example, a push-button switch, a toggle switch, slide switch, a rotatable knob, and a touch panel. The control circuitry may also comprise a microphone configured to receive verbal commands from a user and/or detect ambient noise. The control circuitry may also be configured to control the light beacon to emit one of a constant light or a flashing light, and when in a flashing light mode, the control circuitry may be used to adjust a duty cycle of the flashing light.

The control circuitry may be configured to control the light beacon to flash at a default duty cycle when the light beacon is turned on and the light beacon is set to a flashing light mode. The control circuitry may be configured to control the light beacon to flash at a previously set duty cycle when e light beacon is turned on and the light beacon is set to a flashing light mode.

Other examples of the disclosure may have the control circuitry is configured to control the light beacon to emit different colors of light. For example, the control circuitry may be configured to control the light beacon to emit one of the different colors of light at a time, where there may be a period of time where a first color of light may be emitted for a first period of time and a second color of light may be emitted for a second period of time. There may also be a third period of time between the first period of time and the second period of time when no light is emitted by the light beacon.

The protection device may also comprise a speaker configured to output a warning sound, where the control circuitry is configured to output the warning sound when the light beacon is turned on. The control circuitry may also be configured to adjust a volume of the speaker and/or select one of a plurality of different warning sounds and patterns.

The protection device may have at least a portion of the light beacon is removably coupled to the protection device.

It can also be seen that the disclosure provides for a welding protection device that comprises an eye protection shield, a light beacon configured to emit light in substantially all directions, and a control circuitry configured to control operation of the light beacon. For example, the control circuitry may be configured to perform one or more of: turn on the light beacon at a time when the welding protection device is on a user, turn off the light beacon when the welding protection device is taken off the user, turn on the light beacon when the eye protection shield is in a down position, and turn off the light beacon when the eye protection shield is in an up position As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" When executing a second one or more lines of code. As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g." and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc).

The present methods and/or systems may be realized in hardware, software, or a combination of hardware and software. The present methods and/or systems may be realized in a centralized fashion in at least one computing system or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What are claimed:

1. A protection device, comprising:
   an eye protection shield;
   a light beacon configured to emit light in substantially all directions; and
   a control circuitry to control the light beacon, wherein the control circuitry is configured to control the light beacon to emit one of a constant light or a flashing light.

2. The protection device of claim 1, comprising a visor configured to block at least some light from the light beacon from reaching a light sensor used for an auto-darkening feature for the eye protection shield.

3. The protection device of claim 1, wherein the control circuitry is configured to perform one or both of:
   turn on the light beacon at a time when the protection device is on a user; and
   turn off the light beacon when the protection device is taken off the user.

4. The protection device of claim 1, wherein the control circuitry is configured to:
   turn on the light beacon at a time when the eye protection shield is in a down position; and
   turn off the light beacon when the eye protection shield is in an up position.

5. The protection device of claim 1, wherein the control circuitry comprises one or more of: a push-button switch, a toggle switch, slide switch, a rotatable knob, and a touch panel.

6. The protection device of claim 1, wherein the control circuitry comprises a microphone.

7. The protection device of claim 1, wherein the control circuitry is configured to adjust a duty cycle of the flashing light.

8. The protection device of claim 1, wherein the control circuitry is configured to control the light beacon to flash at a default duty cycle when the light beacon is turned on and the light beacon is set to a flashing light mode.

9. The protection device of claim 1, wherein the control circuitry is configured to control the light beacon to flash at a previously set duty cycle when the light beacon is turned on and the light beacon is set to a flashing light mode.

10. The protection device of claim 1, wherein the control circuitry is configured to control the light beacon to emit different colors of light.

11. The protection device of claim 10, wherein the control circuitry is configured to control the light beacon to emit one of the different colors of light at a time.

12. The protection device of claim 11, wherein the control circuitry is configured to control the light beacon to emit a first color of light for a first period of time and a second color of light for a second period of time.

13. The protection device of claim 12, wherein there is a third period of time between the first period of time and the second period of time when no light is emitted by the light beacon.

14. The protection device of claim 1, comprising a speaker configured to output a warning sound.

15. The protection device of claim 14, wherein the control circuitry is configured to output the warning sound when the light beacon is turned on.

16. The protection device of claim 15, wherein the control circuitry is configured to adjust a volume of the speaker.

17. The protection device of claim 14, wherein the control circuitry is configured to select one of a plurality of different warning sounds and patterns.

18. The protection device of claim 1, wherein at least a portion of the light beacon is removably coupled to the protection device.

19. A welding protection device, comprising:
an eye protection shield;
a light beacon configured to emit light in substantially all directions; and
a control circuitry configured to control operation of the light beacon,
wherein the control circuitry is configured to:
turn on the light beacon at a time when the welding protection device is on a user, and
turn off the light beacon when the welding protection device is taken off the user.

20. A protection device, comprising:
an eye protection shield;
a light beacon configured to emit light in substantially all directions; and
a control circuitry to control the light beacon, wherein the control circuitry is configured to control the light beacon to emit a first color of light for a first period of time and a second color of light for a second period of time, wherein the second color is different from the first color.

* * * * *